US00PP08916P

United States Patent [19]

Drewlow

[11] Patent Number: Plant 8,916

[45] Date of Patent: Sep. 27, 1994

[54] IMPATIENS PLANT NAMED BAROQUE

[75] Inventor: Lyndon W. Drewlow, Ashtabula, Ohio

[73] Assignee: Mikkelsens, Inc., Ashtabula, Ohio

[21] Appl. No.: 163,768

[22] Filed: Dec. 9, 1993

[51] Int. Cl.[5] ..... A01H 5/00

[52] U.S. Cl. ..... Plt./87.6

[58] Field of Search ..... Plt. 87.6

[56] References Cited

U.S. PATENT DOCUMENTS

PP 7241 6/1990 Drewlow ..... Plt./87.6

*Primary Examiner*—James R. Feyrer

*Attorney, Agent, or Firm*—Foley & Lardner

[57] ABSTRACT

A new and distinct cultivar of Impatiens plant named Baroque, characterized by its double-flower form having ten petals, purple rose flower color, flower diameter of 4.5 to 5.0 cm, light-green to pinkish-red flower spur, green pedicels, six leaves in a whorl, continuous flowering above leaf canopy, medium-green foliage with light-green midrib, semi-compact growth habit, highly self-branching and floriferous habit, ability to tolerate both high and low temperatures, and its adaptability to production in 10 cm up to 15–25 cm pots.

2 Drawing Sheets

The present invention relates to a new and distinctive cultivar of Impatiens plant, botanically known as Impatiens, commercially known as New Guinea Impatiens, and known by the cultivar name Baroque.

The new cultivar was developed in a controlled breeding program conducted by the inventor Lyndon W. Drewlow in Ashtabula, Ohio. Baroque was created by crossing Mikkelsen Seedling No. 90-1043-2 (seed parent) with Mikkelsen Seedling No. 90-1172-2 (pollen parent). Both parents are proprietary cultivars used in the breeding program.

Asexual reproduction by terminal or stem cuttings, carried out by or under the supervision of the inventor at Ashtabula, Ohio, has shown that the unique features of this new impatiens are stabilized and are reproduced true to type in successive propagations.

The following combination of characteristics distinguish the new Impatiens from both its parent varieties and other cultivated impatiens of this type known and used in the floriculture industry. The description includes reference to comparison cultivars Antares, disclosed in U.S. Plant Pat. No. 7,241 and Canon, disclosed in a pending application of this inventor.

1. Baroque is a representative of an entirely new class of New Guinea impatiens that have ten flower petals, which is double the number of petals of the single flower five petal types such as Antares. Canon is another cultivar in the double-flowered group.

2. Baroque is purple rose in flower color (80C) while Antares is a deeper lavender-purple (between 72C and 77B) in color.

3. Baroque has a flower diameter of 4.5 to 5.0 cm, the same as Canon, and larger than Antares which as a 4.0 to 4.5 cm flower diameter.

4. The flower spur of Baroque is light green near the major sepal and pinkish-red in the lower two-thirds to three-fourths of the spur. The entire spur of Antares is reddish purple, and Canon has a light green flower spur. All three cultivars have a green tip on the spur.

5. The flower pedicels of Baroque are green in color and hirsute, while Antares has a reddish cast and is glabrous, and Canon has green glabrous pedicels.

6. All three cultivars have similar leaf length at 9 cm but Baroque and Canon have wider leaves at 3.0 to 3.5 cm, with Antares being narrower at 2 to 3 cm. Antares and Baroque both have hirsute upper leaf surfaces while Canon has a glabrous upper surface. Baroque and Canon have solid green leaves while Antares has cream variegation around the midrib under high light conditions.

7. Main and lateral stems of Baroque are hirsute and reddish purple in color. The stems of Antares and Canon are glabrous and have only a reddish tint which is heaviest at the nodes.

8. Baroque is 5 to 7 days later to bloom than Antares sinc it takes the double flower longer to develop and open. Canon is similar in bloom date to Baroque.

9. Baroque usually has six leaves in a whorl, compared to 4 to 5 for Antares and 5 to 6 for Canon.

10. The anther hood of Baroque is cream while Canon has an anther hood closer to white in color and Antares has a reddish tint near the basal end.

In the photographic drawings, the color photo at the top illustrates in perspective view the overall appearance of Baroque, with the colors being as true as it is reasonably possible to obtain in a color reproduction of this type. The color photo was taken on Sep. 24, 1993 under natural light under 40% saran in a shaded glass greenhouse in Ashtabula, Ohio on a sunny day. The black and white photo on the bottom shows three (3) views of a typical flower of the new cultivar.

The following is a detailed description of my new cultivar, based on plants produced in greenhouse in Ashtabula, Ohio during the summer season of the year. Plants were gren in 15 cm pots and measurements were taken 18 weeks after rooted cuttings were planted. Height measurements were taken from the soil line of the container. The plants were grown at 65°–68° F. night temperatures under 3000–4000 foot candles of light, and at 250 ppm nitrogen, 75 ppm potassium, and 250 ppm phosphorous nutritional levels, with trace elements added. Habit of growth, foliage coloration, leaf variegation, size of leaves and flower size will be influenced by nutritional and environmental conditions, without, however, any variance in the genotype.

Color references are made to The Royal Horticultural Society Colour Chart except where general terms of ordinary dictionary significance are used.

Parentage: A controlled cross between female parent Mikkelsen Seedling No. 90-1043-2 and male parent Mikkelsen Seedling 90-1172-2.

Propagation:

(A) *Type cutting.*—Stem tip is 15 mm long and will develop 4 to 5 cm long in 18 to 21 days.

(B) *Time to root.*—8–10 days at 23° C. summer; 10–12 days at 20° C. winter.

(C) *Rooting habit.*—Heavy, fibrous.

Plant description:

(A) *Form and habit of growth.*—Highly self-branched, mounded; semi-compact; continuous flowering, flowers are above leaf canopy; vigorous growing, flowering herb.

(B) *Foliage description.*—Medium green with light-green midrib and major veins. Petiole near attachment to stem, on older leaves especially, shows red tint. No variegation. (1) Size: 9 to 10 cm long and 3.0 to 3.5 cm wide for average mature leaf. (2) Shape: Lanceolate with acuminate apex and acute base. (3) Texture: Top has very short stiff hairs (hirsute) and bottom is glabrous. (4) Margin: Slightly serrate with fine ciliate. (5) Color: Young foliage, top side is between 146A and 147A, under side is 146C; Mature foliage, top side is 147A, under side is 147C. (6) Veination: Pinnate, light green in color.

Flowering description:

(A) *Flowering habits.*—Flowering is continuous from leaf whorl in a progressively orderly manner, with one flower per leaf axil. When the last flower in a leaf whorl opens the first flower in the leaf whorl above starts to open. It takes 5 to 7 days for a mature bud to fully open and the flower may last two weeks or longer depending on environment.

(B) *Natural flowering season.*—Indeterminant and continuous, quantity of flowering increases with increasing levels of light.

(C) *Flower buds.*—Ellipsoidal, flowers perfect; green spur with reddish tint up to 3.5 cm long, with deeper green tip on a mature bud. The throat is behind the ovary and originates from the major sepal.

(D) *Flowers borne.*—On individual hirsute 3.5 cm long green pedicels from a whorl of usually six leaves, flowering progressively around the whorl as buds and leaves develop. One flower per leaf axil is normal.

(E) *Quantity of flowers.*—Highly floriferous because of highly self-branching nature of plant, long-lasting flowers, and full appearance of double flowers.

(F) *Diameter of flower.*—4.5 to 5.0 cm.

(G) *Petals.*—(1) Shape: Heart, keel petals of bottom whorl of petals are largest. (2) Color: Top side in summer when opening is 80C with small 155D white area around eye, fading to 80D with 155D white area around eye; under side is 80D. (3) Number of petals: Ten. (4) Size of petals: Standard: Standard petal in lower whorl is normal while standard petal is upper whorl has characteristics of both standard and keel petals. Wings: Two sets of wing petals with lower larger than upper whorl. Keel: Two sets of normal keel petals, with set on lower whorl being larger than set on upper whorl.

(H) *Reproductive organs.*—(1) Stamens: Five (5) in number. (a) Anther: Hooded shape; color is cream. (b) Pollen color: Cream. (2) Pistils: (a) Stigma shape: Five (5), segmented column; color is whitish green. (b) Style color: Whitish green. (c) Ovaries: Five (5) in number; size is 3 mm when mature; color is deep green.

Disease resistance: No significant insect or disease problems to date.

OTHER IMPORTANT CHARACTERISTICS

1. The self-branching characteristic and semi-compact growth habit of Baroque make it suitable for 10 cm pot production, but cultivar is vigorous enough for 15 and 25 cm pot production as well.

2. Baroque can withstand both high temperatures and sunlight as well as low temperatures (40° to 50° F.), thus, extending the growing season and locations where cultivar can be planted.

3. The ten flower petals result in a fuller looking flower as compared to the normal five petals. Thus, a double-flowered plant with the same number of flowers as a single-flowered plant will appear substantially more colorful.

I claim:

1. A new and distinct cultivar of Impatiens plant named Baroque, as illustrated and described.

* * * * *

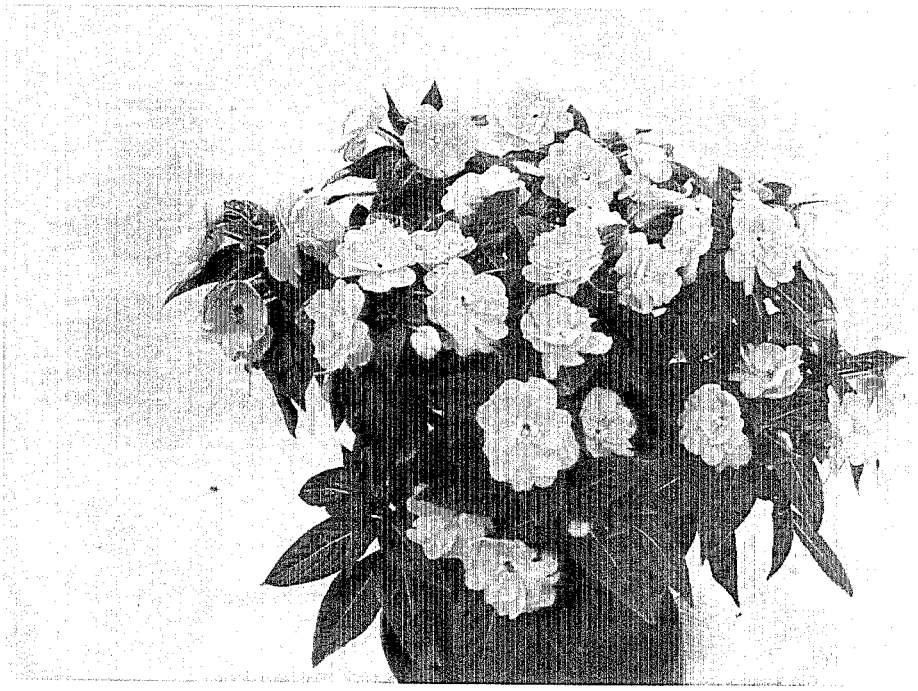

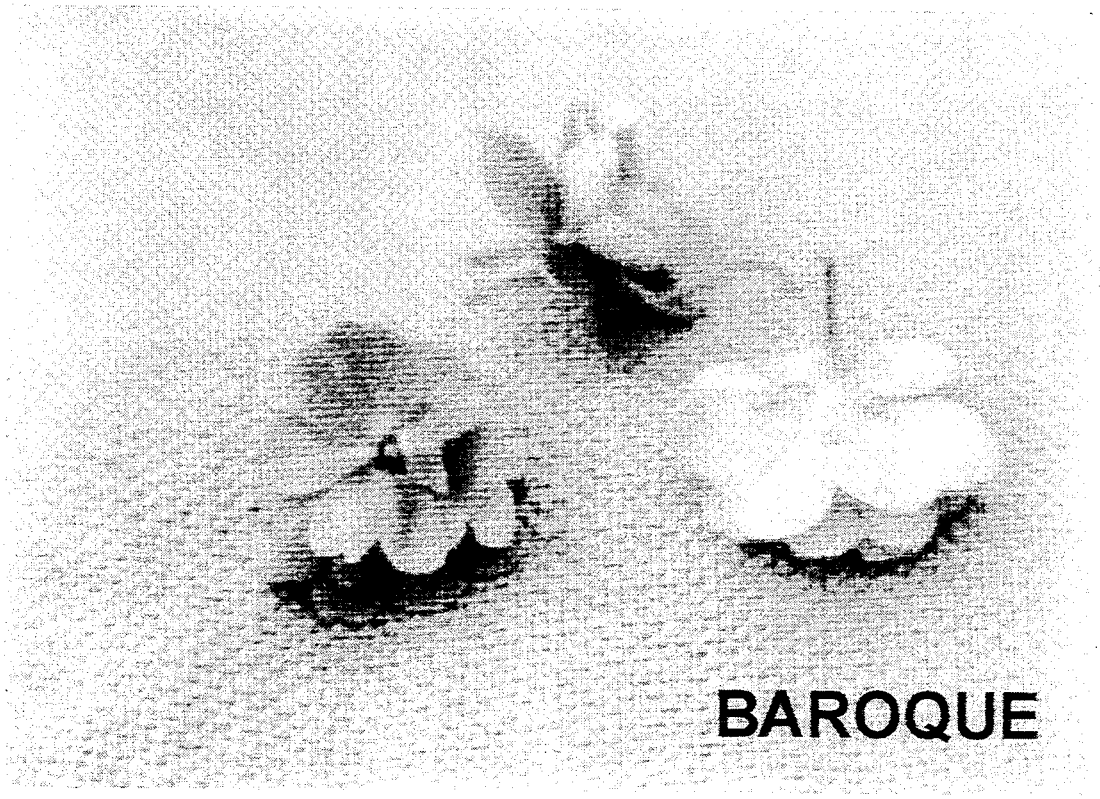
BAROQUE